(12) United States Patent
Schlichte et al.

(10) Patent No.: US 8,381,576 B2
(45) Date of Patent: Feb. 26, 2013

(54) EXPLOSION-PROOF GAS SENSOR WITHOUT PRESSURE-PROOF HOUSING

(75) Inventors: Mladen Schlichte, Lübeck (DE); Jürgen Osswald, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 476 days.

(21) Appl. No.: 12/630,291

(22) Filed: Dec. 3, 2009

(65) Prior Publication Data

US 2010/0192675 A1 Aug. 5, 2010

(30) Foreign Application Priority Data

Feb. 3, 2009 (DE) .......................... 10 2009 007 279

(51) Int. Cl.
*G01N 7/00* (2006.01)
(52) U.S. Cl. ...................................... 73/31.06
(58) Field of Classification Search .................. 73/31.05
See application file for complete search history.

(56) References Cited

U.S. PATENT DOCUMENTS

| | | | | |
|---|---|---|---|---|
| 3,771,960 A | * | 11/1973 | Kim et al. ..................... | 436/152 |
| 4,305,724 A | * | 12/1981 | Micko ........................... | 436/156 |
| 4,560,585 A | | 12/1985 | Khilnani | |
| 4,656,863 A | * | 4/1987 | Takami et al. ................ | 73/31.05 |
| 2006/0243029 A1 | * | 11/2006 | Lange et al. ................. | 73/31.05 |

FOREIGN PATENT DOCUMENTS

| | | |
|---|---|---|
| CH | 638636 A5 | 9/1983 |
| DE | 38 10 409 A1 | 2/1989 |
| DE | 202004018400 U1 | 2/2005 |
| DE | 202004015181 U1 | 2/2006 |
| DE | 102005020131 B3 | 5/2006 |
| DE | 102005003049 B3 | 6/2006 |
| DE | 102006054505 A1 | 5/2008 |
| EP | 1081493 A1 | 3/2001 |
| GB | 2450970 | 1/2009 |
| JP | 57141543 A | 9/1982 |
| WO | WO 0043765 A1 | 7/2000 |

* cited by examiner

*Primary Examiner* — Hezron E Williams
*Assistant Examiner* — Mark A Shabman
(74) *Attorney, Agent, or Firm* — McGlew and Tuttle, P.C.

(57) ABSTRACT

A gas sensor is provided for use in a hazardous explosive atmosphere present continuously or for a long time. The gas sensor is not provided with a pressure-proof housing and is provided with at least one catalytic or semiconductor measuring element (3) in a hollow body (6) defining the measuring element (3) against the environment. The hollow body has breathing openings (4) and wherein the ratio of the area of the breathing openings to the total area of the hollow body equals, furthermore, at most 0.8 or the hollow body is porous with a porous hollow body material having a pore size according to ISO 4003 equal to at most 2 mm.

19 Claims, 1 Drawing Sheet

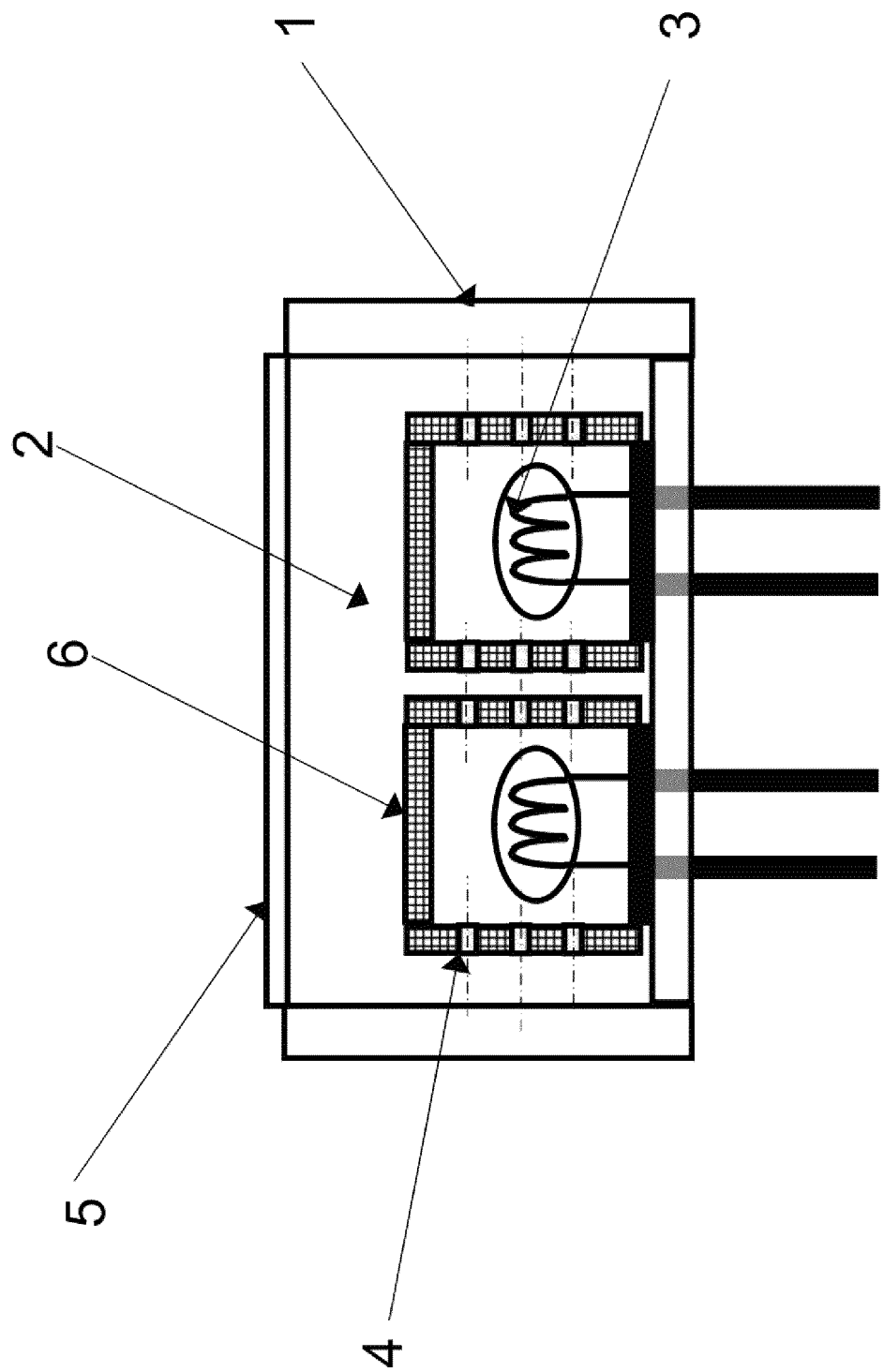

EXPLOSION-PROOF GAS SENSOR WITHOUT PRESSURE-PROOF HOUSING

CROSS REFERENCE TO RELATED APPLICATIONS

This application claims the benefit of priority under 35 U.S.C. §119 of German Patent Application DE 10 2009 007 279.9 filed Feb. 3, 2009, the entire contents of which are incorporated herein by reference.

FIELD OF THE INVENTION

The present invention pertains to an explosion-proof gas sensor for measuring the concentrations of combustible and usually toxic gases or vapors in gas mixtures with at least one catalytic measuring element or with a gas-sensitive semiconductor element in a housing not encapsulated in a pressure-proof manner, wherein the gas sensor or the sensor housing requires no flame trap and can be used in an explosive atmosphere.

BACKGROUND OF THE INVENTION

A gas sensor with a heated gas-sensitive semiconductor element as the measuring element is known, for example, from DE 38 10 409 A1. One essential drawback of this prior-art arrangement is the poorer diffusion of the gas to be measured compared to the prior-art arrangements with support wires and catalytic measuring elements arranged thereon, i.e., especially to heat tone sensors called pellistors. The jacketing of the measuring elements represents an additional diffusion barrier. The gas-sensitive semiconductor elements or heat tone detector elements used to measure the concentrations of combustible or explosive and usually also toxic gases, vapors or gas mixtures contain hot components such as pellistors, whose hot surfaces may ignite an explosive gas mixture or gas-air mixture under operating conditions or in case of a defect. To avoid such life-threatening ignitions, which trigger explosions, by hot surfaces in the gas sensor, such sensors are designed with the "pressure-proof housing" type of protection according to the IEC/EN 60079-1 standard specification.

This means that, on the one hand, the power consumption of such sensors is limited by the actuating electronics thereof, so that the maximum surface temperature of the sensor housing is limited to a certain value.

On the other hand, a flame trap, which is integrated in the sensor housing and which is also used at the same time as a breathing means for the necessary entry of the gas or gases to be measured and the removal of the combustion products formed from the gas sensor, prevents the flame from spreading because of an ignition at hot measuring elements from the sensor housing. Even though the gas sensors, which are designed only according to the "pressure-proof housing" type of protection, may be used in areas in which a hazardous explosive atmosphere may be expected to be occasionally present, they may not be used in areas in which a hazardous explosive atmosphere is present continuously or for a long time.

SUMMARY OF THE INVENTION

The object of the present invention is to provide a gas sensor having at least one catalytic measuring element or a gas-sensitive semiconductor element without pressure-proof housing for measuring explosive gases or gas mixtures in a hazardous explosive atmosphere present continuously or for a long time, without a flame trap being necessary for the gas sensor.

According to the invention, a gas sensor is provided without pressure-proof housing. The sensor comprises a catalytic or semiconductor measuring element and a hollow body with the measuring element disposed therein. The hollow body defines a measuring element extent and comprises a hollow body surface with a surface total area against the environment with breathing openings. A ratio of the area of the breathing openings to the total area of the hollow body equals at most 0.8.

The volume within the hollow body may advantageously equal at most 350 mm$^3$. A ratio of the area of the breathing openings to the total area of the hollow body may advantageously range from 0.01 to 0.8.

The semiconductor measuring element may advantageously comprise a metal oxide semiconductor. The metal oxide semiconductor may advantageously consist of $SnO_2$ or ZnO. The semiconductor may advantageously have a cylindrical and especially regular cylindrical shape.

The hollow body may consist of metal, plastic, ceramic or glass fibers. The hollow body may advantageously contain compounds of Cu, Pb, Pt, Ag, Sn, Zn, Si and/or K for the retention of sulfur- and halogen-containing compounds as well as of organosilicon and lead compounds.

The gas sensor may further comprise a sensor housing wherein the hollow body with measuring element is arranged therein. The sensor housing comprises a covering protective element with mechanical protective action, wherein the protective element comprises one or more of a wire mesh, a perforated plate, a grid and a sintered metal element.

According to another aspect of the invention, a gas sensor without pressure-proof housing is provided. The sensor again comprises a catalytic or semiconductor measuring element and a hollow body. However, the hollow body is a porous hollow body with the measuring element disposed therein. The porous hollow body defines a measuring element extent and comprises a porous hollow body material having a pore size according to ISO 4003 equal to at most 2 mm.

According to still another aspect of the invention, a process is provided for gas sensing in a hazardous explosive atmosphere that is present continuously or for a long time. The process comprises providing a gas sensor without pressure-proof housing wherein the sensor comprises a catalytic or semiconductor measuring element and a hollow body that is one of: a hollow body with the measuring element disposed therein, the hollow body defining a measuring element extent and comprising a hollow body surface with and surface total area against the environment with breathing openings, wherein a ratio of the area of the breathing openings to the total area of the hollow body equals at most 0.8; and a porous hollow body with the measuring element disposed therein, the porous hollow body defining a measuring element extent and comprising a porous hollow body material having a pore size according to ISO 4003 equal to at most 2 mm. The process further comprises positioning the sensor in the hazardous explosive atmosphere; and sensing concentrations of one or more gases present in the hazardous explosive atmosphere.

Improved dissipation of heat into the environment is achieved with controlled diffusion to the sensor element with the proposed design embodiment of the gas sensor according to the invention, with the consequence of a reliable prevention of ignition in the sensor, without the quality of measurement being compromised by the limited gas exchange.

One exemplary embodiment of the present invention will be explained by means of the sole FIGURE. The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

BRIEF DESCRIPTION OF THE DRAWINGS

In the drawings:

The only FIGURE is a vertical sectional view through a sensor arrangement shown schematically with two heat tone sensors.

DESCRIPTION OF THE PREFERRED EMBODIMENTS

Referring to the drawing in particular, one active measuring element 3 and one inactive hot measuring element 3 each are located in a sensor space defining cylindrical hollow body 6 with electric contacts or contact pins, which are shown in the lower area in the FIGURE. The power consumption of the heat tone sensors/pellistors being used is 100 mW to 150 mW during operation at normal rating.

The inner volume of each hollow body 6 equals at most 350 $mm^3$. The hollow bodies 6 consist in the example of metal, plastic, ceramic or gas fibers and have, for example, six lateral holes and/or holes arranged on the front side on the hollow body 6 as breathing openings 4. The material of the hollow body may contain compounds of Cu, Pb, Pt, Ag, Sn, Zn, Si for the retention of sulfur- and halogen-containing substances as well as of organosilicon and lead compounds, which may damage the measuring element or measuring elements 3. The breathing openings 4 may also be formed, as an alternative, by pores in the material of the hollow body.

The ratio of the area of the breathing openings 4 to the total area of the hollow body 6 ranges from about 0.01 to a maximum of 0.8.

If the hollow body 6 consists of an inherently porous material in an alternative embodiment, the maximum pore size of the material of the hollow body according to the method described in ISO 4003 is 2 mm.

The inner volume 2 of the combustion chamber may be, for example, in the range of 500 to 2,000 $mm^3$.

The gas or gas mixture to be measured diffuses into the hollow bodies 6. Both measuring elements 3 are heated, and one measuring element 3 is coated catalytically, so that the gas to be measured is burned in a controlled manner. The oxygen needed for the combustion is extracted from the ambient air. The catalytically coated measuring element 3 is additionally heated by the heat of combustion formed. The heating leads to a measurable change in the resistance of the measuring element 3, which is proportional to the partial pressure of the explosive gas to be measured. The second measuring element 3, which otherwise has the same design, is likewise heated, but is catalytically inactive and is used as a compensator element in an analysis circuit known per se, especially in a bridge circuit.

The cover-like protective element 5 closes the outer sensor housing 1 only mechanically and consists, for example, of a wire mesh element or a sintered metal element.

Improved transport of heat from the environment of the measuring elements 6 as well as controlled diffusion of the explosive gases to be measured to the measuring element or measuring elements 6 are achieved with the proposed design of the gas sensor arrangement, without the design features of the complicated pressure-proof and explosion-proof housing that was hitherto necessary, i.e., without flame trap and without pressure-proof cable ducting into the sensor housing 1.

While specific embodiments of the invention have been described in detail to illustrate the application of the principles of the invention, it will be understood that the invention may be embodied otherwise without departing from such principles.

What is claimed is:

1. A gas sensor without pressure-proof housing, the sensor comprising:
    a catalytic or semiconductor measuring element; and
    a hollow body with the measuring element disposed therein, said hollow body defining a measuring element extent and comprising a hollow body surface with a surface total area against the environment with breathing openings, wherein a ratio of the surface area of the breathing openings to the total surface area of the hollow body equals at most 0.8, wherein a volume within the hollow body equals at most 350 $mm^3$, said breathing openings being through holes, each of said through holes extending continuously from an outer side of said hollow body to an inner side of said hollow body, wherein said through holes are in communication with the environment and an interior of said hollow body.

2. A gas sensor in accordance with claim 1, wherein the ratio of the area of the breathing openings to the total area of the hollow body ranges from 0.01 to 0.8.

3. A gas sensor in accordance with claim 2, wherein the semiconductor measuring element comprises a metal oxide semiconductor.

4. A gas sensor in accordance with claim 3, wherein the metal oxide semiconductor consists of $SnO_2$ or $ZnO$.

5. A gas sensor in accordance with claim 2, wherein the semiconductor has a cylindrical and especially regular cylindrical shape.

6. A gas sensor in accordance with claim 2, wherein the hollow body consists of metal, plastic, ceramic or glass fibers.

7. A gas sensor in accordance with claim 2, wherein the hollow body contains compounds of one or more of Cu, Pb, Pt, Ag, Sn, Zn, Si and K for the retention of sulfur- and halogen-containing compounds as well as of organosilicon and lead compounds.

8. A gas sensor in accordance with claim 2, further comprising:
    a sensor housing; and
    another hollow body with another measuring element disposed therein, said hollow body with said another measuring element arranged therein being arranged in said sensor housing, said another hollow body defining another measuring element extent and comprising another hollow body surface with another surface total area against the environment with additional breathing openings, wherein a ratio of the another surface area of the additional breathing openings to the total another surface area of the another hollow body equals at most 0.8, said another hollow body being in communication with said hollow body via said additional breathing openings and said breathing openings, wherein:
    the hollow body with measuring element arranged therein is arranged in the sensor housing, said hollow body being located at spaced location from said another hollow body, said measuring element comprising a catalytic coating, said another measuring element being catalytically inactive, wherein a volume within the another hollow body equals at most 350 mm³;
the sensor housing comprises a covering protective element with mechanical protective action, wherein the protective element comprises one or more of a wire mesh, a perforated plate, a grid and a sintered metal element.

9. A gas sensor without pressure-proof housing, the sensor comprising:
a catalytic or semiconductor measuring element;
a porous hollow body with the measuring element disposed therein, said porous hollow body defining a measuring element extent and comprising a porous hollow body material having a pore size according to ISO 4003 equal to at most 2 mm, wherein a volume within the hollow body equals at most 350 mm³.

10. A gas sensor in accordance with claim 9, wherein the semiconductor measuring element comprises a metal oxide semiconductor.

11. A gas sensor in accordance with claim 10, wherein the metal oxide semiconductor consists of $SnO_2$ or ZnO.

12. A gas sensor in accordance with claim 9, wherein the semiconductor has a cylindrical and especially regular cylindrical shape.

13. A gas sensor in accordance with claim 9, wherein the hollow body consists of metal, plastic, ceramic or glass fibers.

14. A gas sensor in accordance with claim 9, wherein the hollow body contains compounds of one or more of Cu, Pb, Pt, Ag, Sn, Zn, Si and K for the retention of sulfur- and halogen-containing compounds as well as of organosilicon and lead compounds.

15. A gas sensor in accordance with claim 9, further comprising:
a sensor housing; and
another hollow body with another measuring element disposed therein, said hollow body with said another measuring element disposed therein being arranged in said sensor housing, said another hollow body defining another measuring element extent and comprising another hollow body surface with another surface total area against the environment with additional breathing openings, wherein a ratio of the another area of the additional breathing openings to the total another area of the another hollow body equals at most 0.8, wherein:
the hollow body with measuring element arranged therein is arranged in the sensor housing, said hollow body being located at spaced location from said another hollow body, said hollow body being in communication with said another hollow body via said additional breathing openings and said breathing openings, said measuring element comprising a catalytic coating, said another measuring element being catalytically inactive, wherein a volume within the another hollow body equals at most 350 mm³;
the sensor housing comprises a covering protective element with mechanical protective action, wherein the protective element comprises one or more of a wire mesh, a perforated plate, a grid and a sintered metal element.

16. A process for gas sensing in a hazardous explosive atmosphere that is present continuously or for a long time, the process comprising:
providing a gas sensor without pressure-proof housing, the sensor comprising: a catalytic or semiconductor measuring element and one of:
a hollow body with the measuring element disposed therein, said hollow body defining a measuring element extent and comprising a hollow body surface with a surface total area against the environment with breathing openings, wherein a ratio of the area of the breathing openings to the total area of the hollow body equals at most 0.8; and
a porous hollow body with the measuring element disposed therein, said porous hollow body defining a measuring element extent and comprising a porous hollow body material having a pore size according to ISO 4003 equal to at most 2 mm;
positioning the sensor in the hazardous explosive atmosphere, wherein a volume within said one of said porous hollow body and said hollow body equals at most 350 mm³; and
sensing concentrations of one or more gases present in the hazardous explosive atmosphere.

17. A process in accordance with claim 16, further comprising:
providing a sensor housing; and
providing one of another hollow body and another porous hollow body;
providing another measuring element disposed in said one of another hollow body and another porous hollow body, said one of another hollow body and another porous hollow body with said another measuring element disposed therein being arranged in said sensor housing, said one of another hollow body and another porous hollow body defining another measuring element extent and comprising another hollow body surface with another surface total area against the environment with additional breathing openings, wherein a ratio of the another surface area of the additional breathing openings to the total another surface area of the one of another hollow body and another porous hollow body equals at most 0.8, said one of another hollow body and another porous hollow body being located at spaced location from said one of said hollow body and said porous body.

18. A process in accordance with claim 17, wherein said sensor housing comprises a covering protective element with mechanical protective action, wherein the protective element comprises one or more of a wire mesh, a perforated plate, a grid and a sintered metal element, said measuring element comprising a catalytic coating, said another measuring element being catalytically inactive.

19. A process in accordance with claim 18, wherein each of said additional breathing openings of said another hollow body is aligned with one or more of said breathing openings of said hollow body, wherein a volume within said one of said porous hollow body and said hollow body equals at most 350 mm³.

* * * * *